US00PP12807P2

(12) United States Plant Patent
Trees

(10) Patent No.: US PP12,807 P2
(45) Date of Patent: Jul. 30, 2002

(54) VERBENA PLANT NAMED 'BALAZDAPI'

(75) Inventor: Scott C. Trees, Shell Beach, CA (US)

(73) Assignee: Ball Florapoint, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/808,204

(22) Filed: Mar. 14, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named 'Balazdapi', characterized by its dark purple flowers, mounded trailing habit, and dark green leaves.

1 Drawing Sheet

BACKGROUND OF INVENTION

The present invention comprises a new and distinct verbena plant, botanically known as *Verbena hybrida*, and hereinafter referred to by the cultivar name 'Balazdapi'.

The new cultivar was developed by the inventor through a controlled breeding program during 1998, at Arroyo Grande, Calif. The objective of breeding program was the development of verbena cultivars with semi-trailing mounded habit, continuous flowering, excellent basal branching and small, dark green foliage.

The female (seed) parent of 'Balazdapi' was the commercially available seed verbena 'Quartz Blue' (unpatented), which exhibits dark purple flowers with white "eye", upright growth habit and medium green foliage. The male (pollen) parent of 'Balazdapi' was the commercially available verbena 'Temari Violet' (unpatented) which exhibits dark lavender flowers, a trailing growth habit and medium green foliage.

Asexual reproduction of the new cultivar by terminal cuttings in Arroyo Grande, Calif. and West Chicago, Ill. has demonstrated that the characteristics of the new cultivar as herein described are firmly fixed and retained through successive generations of such asexual propagation.

SUMMARY OF INVENTION

It was found that the cultivar of the present invention:

(a) exhiits dark purple flowers, (b) forms dark green serrate foliage, (c) exhibits a good basal branching character and (d) exhibits an upright mounded and trailing growth habit.

The new cultivar of the present invention can be compared to its male parent, 'Temari Violet'. In side by side comparison, the new cultivar differs from the 'Temari Violet' cultivar by the following characteristics: it is found that the new cultivar has larger leaves, more flowers per inflorescence, petals that are more overlapping and flowers of a different color as detailed in Table A.

When the new cultivar of the present invention is compared to 'Balazlavi' (co-pending U.S. Plant patent application Ser. No. 09/808,318), the new cultivar is distinguished from 'Balazlavi' primarily in petal coloration. When the new cultivar of the present invention is compared to 'Balwilapi' (co-pending U.S. Plant patent application Ser. No. 09/822, 611), the new cultivar is distinguished from 'Balwilapi' primarily in petal coloration.

BRIEF DESCRIPTION OF PHOTOGRAPH

The accompanying photograph illustrates the overall appearance of the new cultivar as true as it is reasonably possible to obtain colored reproductions of this type. Color in the photograph may differ slightly from the color values cited in the detailed botanical description which accurately describe the actual colors of the new Verbena. The photograph comprises a side perspective view of 'Balazdapi'. The plants were grown in a greenhouse at West Chicago, Ill., U.S.A.

DETAILED BOTANICAL DESCRIPTION

The 'Balazdapi' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Aug. 15, 2000. The readings were taken between 1:00 and 3:00 p.m. under natural daylight conditions. The plants used for the descriptions were produced from cuttings taken from stock plants and grown for about 11 weeks after planting rooted cuttings in 10 cm pots in a double poly carbonate covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balazdapi'.

Parentage:

*Male parent.*—'Temari Violet'.

*Female parent.*—'Quartz Blue'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8–10 weeks after the planting of a rooted cutting, commonly measures approximately 29.8 cm in height and approximately 44.8 cm in width.

*Form.*—Upright mounded and trailing.

*Stem.*—Tetragonal, approximately 2 mm in diameter, with dense pubescence, 144B with some reddish anthocyanin pigmentation along edges. Internode length is approximately 2.2 cm.

*Foliage.*—Leaves are opposite, ovate with serrate margin, acute apex, attenuate base, covered with short stiff hairs on upper and lower surface, especially along veins on lower surface, approximately 2.5 cm in length and approximately 1.8 cm at widest point. Upper surface is 137A, lower surface is 137D; venation is 144C for upper and lower surface. Petiole length is 3 mm, color is 144C.

Flowering description:

*Flowering habit.*—Freely flowering.

*Natural flowering season.*—Year round in greenhouse environment. April through October in garden.

*Inflorescence type.*—Corymb, approximately 3.2 cm deep and approximately 5 cm in diameter with approximately 21 fully open flowers per inflorescence at any one time.

*Peduncle.*—Approximately 2 cm in length, 1 mm in diameter, 144B.

*Bud.*—Round, 4 mm in diameter, 86B.

*Petals.*—Five, fused at base, somewhat overlapping, flat.

*Flower diameter.*—Approximately 2.1 cm, corolla tube approximately 2.3 cm long.

*Calyx.*—1.4 cm in length, 2 mm in diameter, 5 toothed, 5 ribbed, with stipules, 144A (both surfaces) with reddish anthocyanin coloration at one spot along rim.

*Flower color.*—Fully opened, upper surface: between 86A and 86B with small area of 155D at base of upper petal and smaller area of 155D at base of lateral and lower petals. Lower surface: 86D with whiskers of 154D surrounding the opening of corolla tube.

*Reproductive organs.*—There are 4 stamens; one pistil; pollen color is 154C.

Seed production: Seed production has not been observed.

Disease resistance: Resistance to pathogens has not been observed.

TABLE A

| CHARACTERISTIC | 'BALAZDAPI' | 'TEMARI VIOLET' |
|---|---|---|
| INTERNODE LENGTH | 2.2 CM | 2.5 CM |
| LEAF LENGTH × WIDTH | 2.5 CM × 1.8 CM | 2 CM × 1.5 CM |
| INFLORESCENCE LENGTH × WIDTH | 3.2 CM × 5 CM | 2.9 CM × 4.3 CM |
| # FLOWERS/INFLORESCENCE | 21 | 16 |
| PETALS | SOMEWHAT OVERLAPPING | NON OVERLAPPING |
| FLOWER COLOR-UPPER SURFACE-RHS | BETWEEN 86A & 86B WITH SMALL AREA OF 155D AT BASE OF UPPER PETAL AND SMALLER AREA OF 155D AT BASE OF LATERAL AND LOWER PETALS | BETWEEN 80A & 81A |
| FLOWER COLOR-LOWER SURFACE-RHS | 86D | 84A AT APEX; 85B AT BASE |
| CALYX LENGTH | 1.4 CM | 1.3 CM |
| CALYX DIAMETER | 2 MM | 1 MM |

I claim:

1. A new and distinct cultivar of *Verbena hybrida* plant named 'Balazdapi' substantially as herein shown and described, which:

(a) exhibits dark purple flowers, (b) forms dark green serrate foliage, (c) exhibits a good basal branching character and (d) exhibits upright mounded and trailing growth habit.

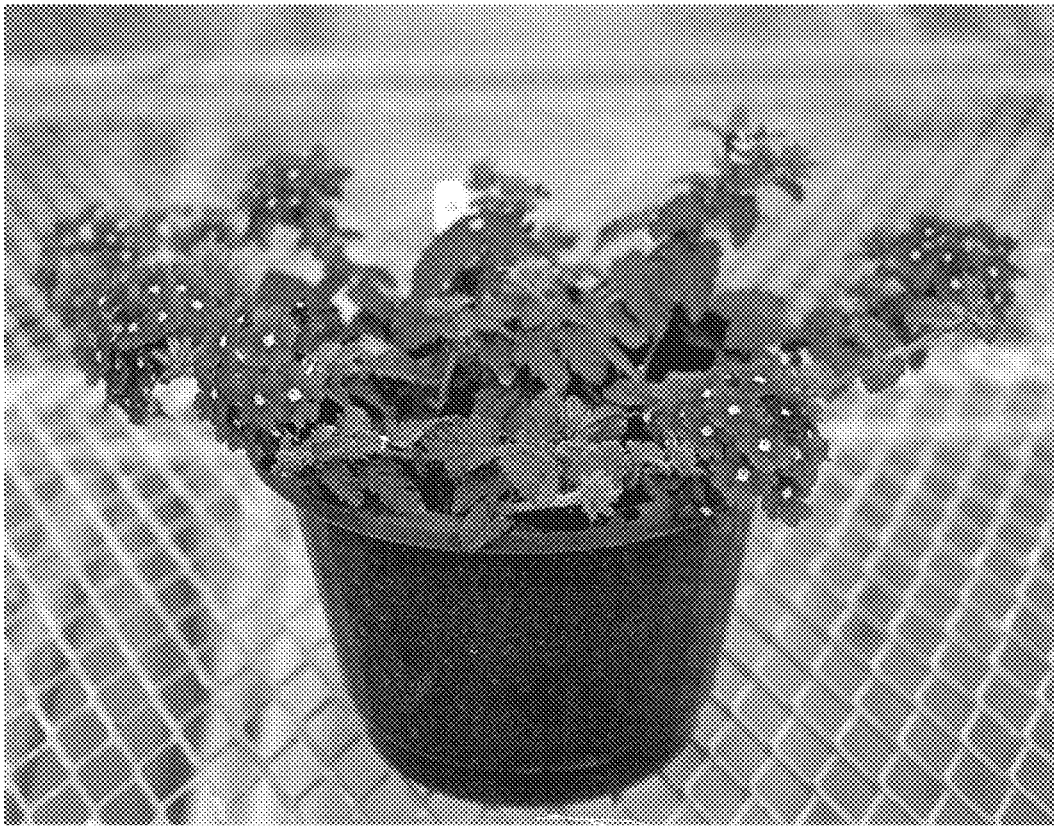

* * * * *